United States Patent
Maruyama

(10) Patent No.: US 6,194,620 B1
(45) Date of Patent: *Feb. 27, 2001

(54) DICHLORO TETRAFLOURO-{2,2}-PARACYCLOPANE, A PROCESS FOR MANUFACTURING THEREOF AND POLY-α, α-DIFLUORO-CHLORO-PARA-XYLYLENE FILM PREPARED THEREFROM

(75) Inventor: Hiroshi Maruyama, Chiba-ken (JP)

(73) Assignee: Daisan Kasei Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/789,012

(22) Filed: Jan. 27, 1997

(51) Int. Cl.$^7$ .............................. C07C 19/08; C07C 22/00; C08G 73/24
(52) U.S. Cl. ......................... 570/127; 570/129; 570/143; 570/144; 570/184; 528/401
(58) Field of Search .................................... 570/184, 129, 570/144, 127, 143; 528/401

(56) References Cited

U.S. PATENT DOCUMENTS

| | | | |
|---|---|---|---|
| 3,221,068 | * | 11/1965 | Gorham . |
| 4,783,561 | * | 11/1988 | Pregaglia et al. ................... 570/184 |
| 4,795,838 | * | 1/1989 | Bornengo et al. ................... 570/184 |
| 4,816,608 | * | 3/1989 | Bornengo et al. ................... 570/184 |
| 4,849,559 | * | 7/1989 | Lee et al. ............................. 570/184 |
| 4,853,488 | * | 8/1989 | Ungarelli et al. ................... 570/184 |
| 5,210,341 | * | 5/1993 | Dolbier et al. ...................... 570/129 |
| 5,536,892 | * | 7/1996 | Dolbier et al. ...................... 570/144 |
| 5,679,874 | * | 10/1997 | Maruyama ........................... 570/184 |

FOREIGN PATENT DOCUMENTS 704 487 * 2/1965 (CA) .................................... 570/129

OTHER PUBLICATIONS

Synthesis of 1,1,9,9–Tetrafluoro [2.2] Paracyclophane and Its Polymerization by Vapor Deposition Method, Takahito Itoh, Siro Okuoka, Masataka Kubo, and Shouji Iwatsuki, Journal of Polymer Science: Part A: Polymer Chemistry, vol. 33, 359–363 (1995).

* cited by examiner

*Primary Examiner*—Alan Siegel
(74) *Attorney, Agent, or Firm*—Smith Gambrell & Russell, LLP

(57) ABSTRACT

Dichloro-tetrafluoro-[2,2]-paracyclophane (formula I), which is a novel compound useful as a material for forming a coating film by chemical vapor deposition, and a process for manufacturing thereof and poly-αα-difluoro-chloro-para-xylylene film prepared therefrom are disclosed. Dichloro-tetrafluoro-[2,2]-paracyclophane is manufactured by chlorinating tetrafluoro-[2,2]-paracyclophane. The film to be formed by chemical vapor deposition of dichloro-tetrafluoro-[2,2]-paracyclophane has remarkably improved thermostability, as compared with the conventional products and is expected to be applied in various fields.

3 Claims, No Drawings

DICHLORO TETRAFLOURO-{2,2}-PARACYCLOPANE, A PROCESS FOR MANUFACTURING THEREOF AND POLY-α, α-DIFLUORO-CHLORO-PARA-XYLYLENE FILM PREPARED THEREFROM

The contents of Japanese patent application 7-254389 filed Aug. 25, 1995, are submitted with and incorporated by reference into this specification.

FIELD OF THE INVENTION

The present invention relates to dichloro-tetrafluoro-[2,2]-paracyclophane (formula I), which is a novel compound useful as a material for forming a coating film by chemical vapor deposition, and a process for manufacturing thereof and poly-αα-difluoro-chloro-para-xylylene film prepared therefrom.

According to the present invention, dichloro-tetrafluoro-[2,2]-paracyclophane (formula I) is manufactured by chlorinating tetrafluoro-[2,2]-paracyclophane of the following formula (II).

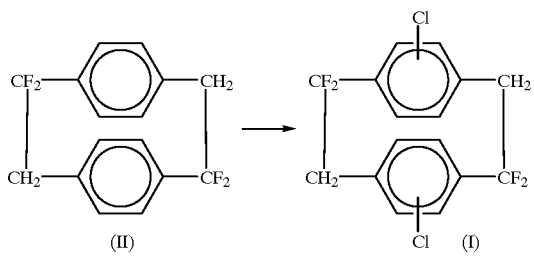

BACKGROUND OF THE INVENTION

[2,2]-paracyclophane and its derivatives of the following general formula (III)

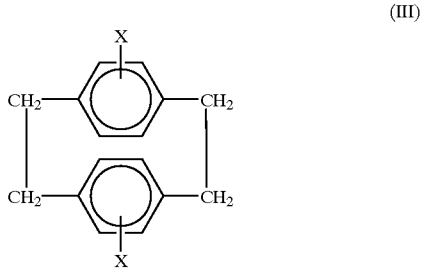

wherein X means a substituent selected from a group consists of hydrogen, chlorine, bromine, fluorine and alkyl;

form a poly-para-xylylene film (including a nucleus-substituted poly-para-xylylene film; and forth) on a substrate by chemical vapor deposition through the following reactions. In the following formula, n means the degree of polymerization:

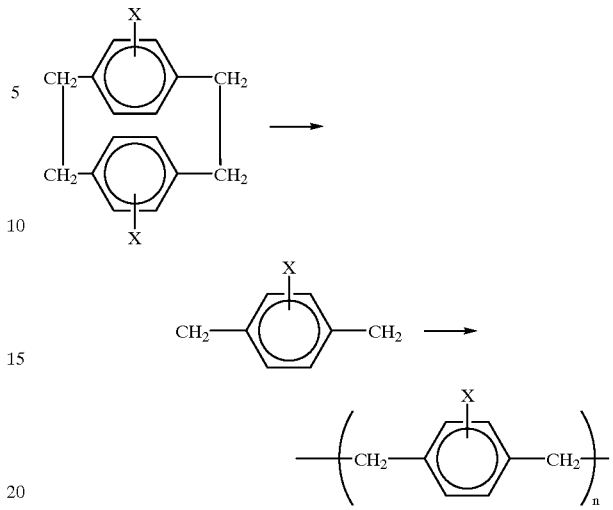

According to this coating method, it is possible to form coating films over substances of all shapes such that the films are true to the shapes, and thus formed polymeric thin films are excellent in gas barrier and electric characteristics and are widely used as materials of electronic parts or for coating of space apparatus.

However, a poly-para-xylylene film prepared from the compound of the above formula (III) has a limit in use in spite of its excellent characteristics. It is that said poly-para-xylylene film, though having a wide application range in vacuum and nitrogen, has a limited application temperature in atmosphere because the structure —$CH_2$—$CH_2$— binding benzene nuclei in its polymeric structure is liable to be oxidized. For example, this poly-para-xylylene film loses flexibility and strength as a film at 200° C. within about 30 minutes in atmosphere to get ragged only by slight rubbing though at variance to some degree with the presence or absence of a substituent of the benzene nuclei and the kind of substituent. As a countermeasure against this, it has been proposed to add an antioxidant into the film (See U.S. Pat. Nos. 4,176,209 5,267,390 and 5,270,082), which however brings no essential solution.

In order to broadly apply the poly-para-xylylene film in various fields, it is required to increase the thermostability of the film in the presence of oxygen.

It is known that a poly-para-xylylene of the following formula in which hydrogens of its methylene group are all substituted by fluorine

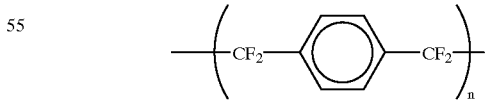

wherein n means the degree of polymerization, has an outstanding thermostability. As to a process for manufacturing octafluoro-[2,2]-paracyclophane which is a starting material for the manufacture of this polymer, there are some patents and a patent application (see U.S. Pat. Nos. 3,268,599 3,274,267 and 3,297,591 and Japanese Patent Laid-open No. 255,149/1993).

However, mass production of these compounds is difficult and the films prepared therefrom have problems in adhering to substrates and the like. The objective of the present invention is to provide a new compound of the formula (I), dichloro-tetrafluoro-[2,2]-paracyclophane, which can be readily produced and is useful to form heat-resistant poly-paraxylylene film. Another objective of the present invention is to provide a highly thermostable poly-para-xylylene film prepared from said new compound.

DETAILED DESCRIPTION OF THE INVENTION

The present inventor intended to change the conventional poly-para-xylylene structure (IV) into a structure (V) (wherein n means degree of polymerization) in which 2 hydrogens of its methylene group on one side were substituted by fluorine as shown in the following structural formula so as to obtain a thermostable polymer in atmosphere. Thus, the inventor tried the synthesis of dichloro-tetrafluoro-[2,2]-paracyclophane (formula I) as a starting material for manufacturing said polymer as well as the polymerization and film formation by chemical vapor deposition thereof.

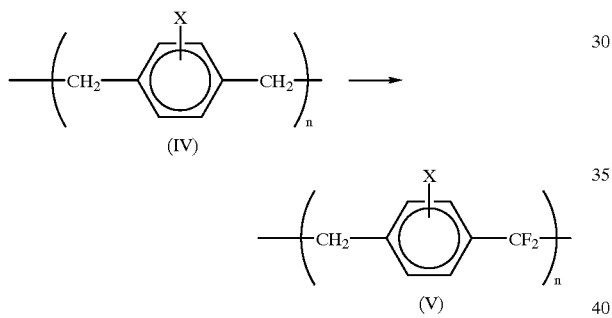

That is, the present invention comprises dichloro-tetrafluoro-[2,2] paracyclophane represented by the above formula (I), a process for manufacturing thereof and poly-α,α-difluoro-chloro-para-xylylene film prepared therefrom. The synthesis and the vapor deposition of this substance have never been tried.

The inventor of the present invention recently filed a patent application concerning tetrafluoro-[2,2]-paracyclophane, a process for manufacturing thereof and poly-α,α-difluoro-para-xylylene film prepared therefrom. The compound of the present invention, which is a dichloro derivative of the compound of the earlier invention, has various advantages over the compound of the earlier invention. For example, it can be coated more easily on a substrate by chemical vapor deposition than the earlier compound and the film prepared therefrom has more improved thermostability in atmosphere than that from the earlier compound. It is also expected that the film of the present invention has more improved characteristics such as gas barrier property than the film of the earlier invention.

As one example of processes, this substance was synthesized through the following route.

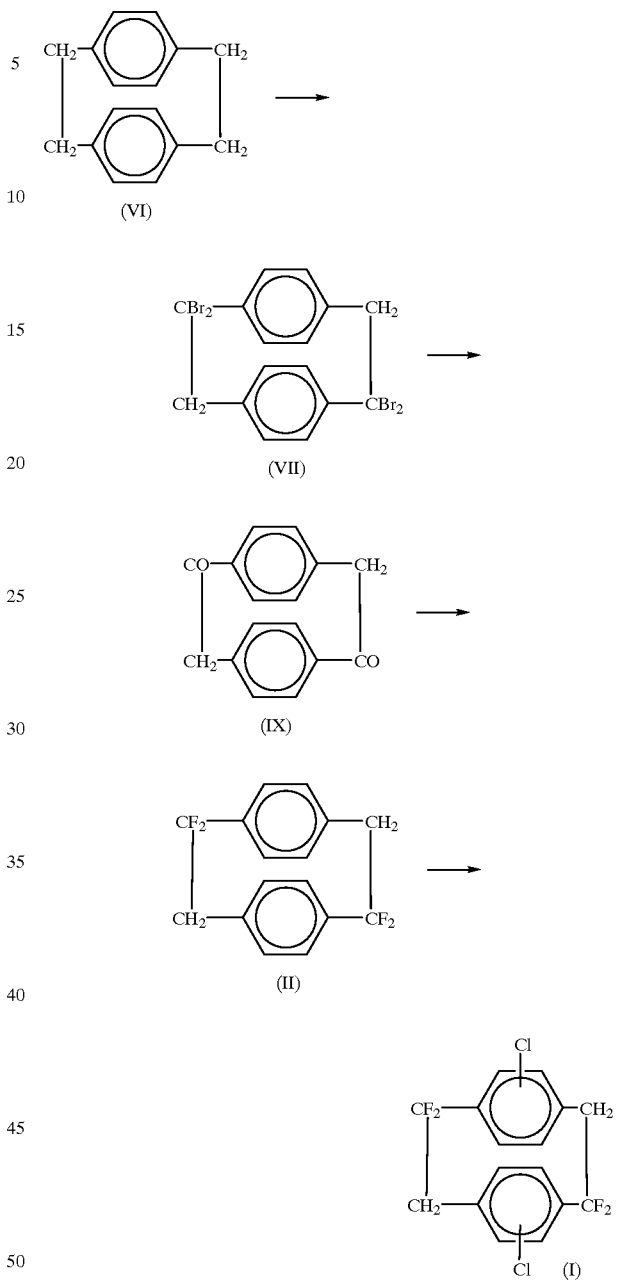

[2,2]-paracyclophane (formula VI) as a starting material is commercially available from Daisan Kasei Co., Ltd.

Tetrabromo-[2,2]-paracyclophane (formula VII) can be obtained by reacting [2,2] paracyclophane (formula VI) with a brominating agent such as N bromosuccinimide or the like in an inert solvent in the presence of a peroxide catalyst or under irradiation with UV light or under interaction of the both. In the bromination, although bromo compounds of the formula (VIII) and the like are also formed other than the aimed product, they can be separated based on the difference of solubility in the solvent.

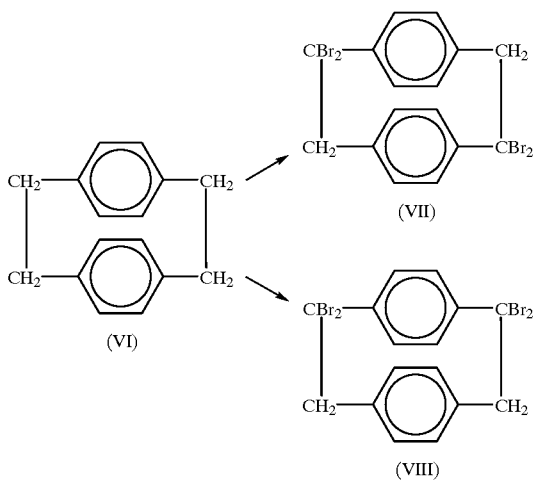

Diketone-[2,2]-paracyclophane (formula IX) can be synthesized by a means of reacting soda acetate, silver acetate or the like with tetra-bromo-[2,2]-paracyclophane in an acetic acid solvent.

Tetrafluoro-[2,2]-paracyclophane (formula II) can be manufactured by reacting a fluorinating agent such as sulfur tetrafluoride, diethylaminosulfur trifluoride (hereinafter described as DAST) or the like with the above ketone compound.

The aimed compound dichloro-tetrafluoro-[2,2]-paracyclophane (formula I) was obtained by chlorination of tetrafluoro-[2,2]-paracyclophane.

The chemical vapor deposition of dichloro-tetrafluoro-[2,2]-paracyclophane (formula I) was carried out in compliance with the conditions which are generally applicable to [2,2]-paracyclophane and its derivatives (formula III), and decomposition of the present substance into radicals, polymerization thereof and film formation were tried.

EXAMPLES

The following Examples serve to illustrate the present invention in more detail. They are, however, not intended to limit its scope in any manner.

Example 1

Synthesis of Tetrabromo-[2,2]-paracyclophane 40.0 g of [2,2]-paracyclophane, 160.0 g of N-bromosuccinimide and 1.1 g of benzoyl peroxide were refluxed to react for 50 hours in 1.51 of carbon tetrachloride solvent with irradiating UV light. The mixture was filtered to remove succinimide and carbon tetrachloride was recovered by distillation. The residue was washed with dichloromethane, recrystallized from chloroform to obtain 14.4 g of tetrabromo-[2,2]-paracyclophane (formula VII). (Decomposition point: 221–223° C.)

Synthesis of Diketone-[2,2]-paracyclophane 14.4 g of the tetrabromo compound synthesized above and 19.2 g of silver acetate were reacted under reflux for 4 hours in 200 ml of acetic acid, followed by addition of 14 ml of water and reaction under reflux for 2 more hours. After completion of reaction, the hot solution was filtered and acetic acid was concentrated, and the precipitate separated by adding water was filtrated. After washing the filtrate with a potassium carbonate aqueous solution and further with water, dried diketone-[2,2]-paracyclophane was obtained. The yield was 5.7 g.

Synthesis of Tetrafluoro-[2,2]-paracyclophane 5.7 g of the diketone compound synthesized above and 9.5 g of DAST were reacted in 100 ml of chloromethane at 30° C. or lower for 22 hours with stirring. Water was added to the reaction mixture to decompose excess DAST, and the dichloromethane solution was successively washed with water, a potassium carbonate aqueous solution and water. After distilling dichloromethane away, the residue was recrystallized from methanol to obtain tetrafluoro-[2,2]-paracyclophane. The yield was 4.9 g (melting point: 196–197° C.). The structure was confirmed by mass spectrometry, nuclear magnetic resonance analysis, etc: $^1$H-NMR (CDCl$_3$, 399.7 MHz, rezol. −0.488 Hz); δ 6.77 ppm (d, 4H, J=8.30 Hz, ArH), 6.67 ppm (d, 4H, J=8.30 Hz, ArH), 3.53 ppm (t, 4H, J=14.65 Hz, CH$_2$)

Synthesis of Dichloro-tetrafluoro-[2,2]-paracyclophane 5.4 g of tetrafluoro-[2,2]-paracyclophane was dissolved in 250 ml of methylene chloride. To this, was added 0.2 g of iron powder and 0.2 g of water and followed by introduction of chlorine gas with stirring. The reaction process was traced by gas chromatography. After the completion of reaction, nitrogen was blown into the reaction mixture to drive out excess chlorine. Then, the reaction solution was washed successively with water and a potassium carbonate aqueous solution. Furthermore, the reaction solution was washed with water until the washing liquid became neutral. After dehydrating the resulting solution over magnesium sulfate, methylene chloride was distilled away. The remaining crystals were recrystallized from methanol to obtain dichloro-tetrafluoro-[2,2]-paracyclophane. The yield was 3.6 g. The structure was confirmed by mass spectrometry.

Formation of Polymer Film by Chemical Vapor Deposition

Dichloro-tetrafluoro-[2,2]-paracyclophane was tried to be vapor-deposited on a glass substrate in compliance with the general vapor deposition conditions applicable to paracyclophane and its derivatives (formula III). As a result of it, the formation of a transparent thin film was confirmed.

Thermostability Test on the Polymer

The thin film formed on a glass substrate by the above chemical vapor deposition was peeled off from the substrate and subjected to thermostability tests. The thermostability tests were carried out according to the following two methods.

(1) Samples were placed in a furnace maintained at 200° C. After a predetermined time, the sample films were examined for their state.

The results of comparison of thermostability among the films from the compound of formula III, tetra-fluoro-[2,2]-para-cyclophane and the present compound are given in Table 1.

TABLE 1

| Starting Material | Polymer Structure | Time | Results |
|---|---|---|---|
| Paracyclophane Formula III: x = H |  | 10 min. | Flexibility and tensile strength were lost. Got ragged by slight rubbing. |
| Dimethyl-Paracyclophane Formula III: x = CH$_3$ | 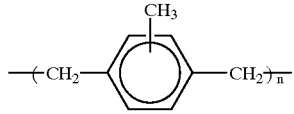 | 10 min. | Flexibility and tensile strength were lost. Got ragged by slight rubbing. |
| Dichloro-Paracyclophane Formula III: x = Cl | 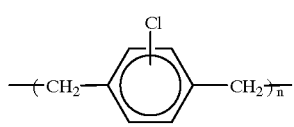 | 20 min. | Flexibility and tensile strength were lost. Got ragged by slight rubbing. |
| tetrafluoro-Paracyclophane Formula II |  | 48 hrs. | Flexibility & tensile strength were maintained. No phenomenon that film got ragged by rubbing was seen. |
| Dichloro-tetrafluoro-Paracyclophane Formula I | 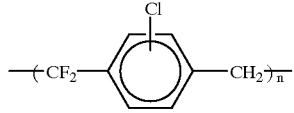 | 48 hrs. | Flexibility & tensile strength were maintained. No phenomenon that film got ragged by rubbing was seen. |

(2) Temperatures at which heat generation by film decomposition is recognized are measured by differential thermal analysis. The results are given in Table 2. Temperatures described in Table 2 indicate those at the time when heat generation reached the maximum peak.

TABLE 2

| Starting Material | polymer Structure | Temperature |
|---|---|---|
| Paracyclophane |  | 222.7° C. (in atmosphere) |
| Dimethyl-paracyclophane | 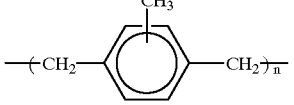 | 224.5° C. (in atmosphere) |
| Dichloro-paracyclophane | 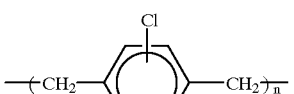 | 253.5° C. (in atmosphere) |
| Tetrafluoro-paracyclophane |  | 383.7° C. (in atmosphere) |
| Dichloro-tetrafluoro-paracyclophane | 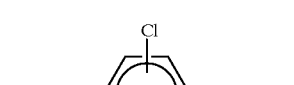 | 500.0° C. or higher (in atmosphere) |

The present invention provide a new compound dichloro-tetrafluro-[2,2]-para-cyclophane which is useful to form poly para-xylylene film having excellnt thermostability and other properties. The film to be formed by chemical vapor deposition of the present product has remarkably improved thermostability, as compared with the conventional products and is expected to be applied in various fields broadly.

What is claimed is:

1. Dichloro-tetrafluoro-[2,2]-paracyclophane of the following formula (I):

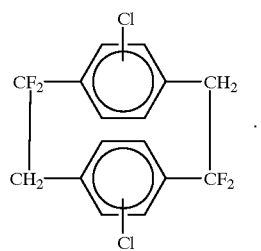

2. A process for manufacturing dichloro-tetrafluoro [2,2] paracyclophane of the formula (I) in claim 1, which comprises chlorinating tetra-fluoro-[2,2]-para-cyclophane of the following formula (II):

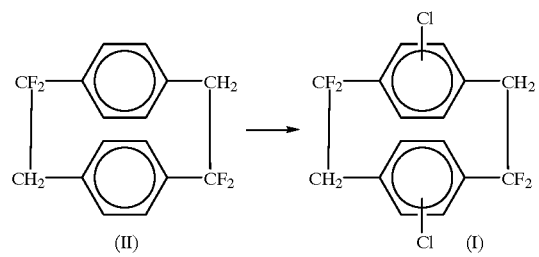

3. Highly regulated thermostable poly-α, α-difluoro-chloro-para-xylylene film having the following structural formula (X):

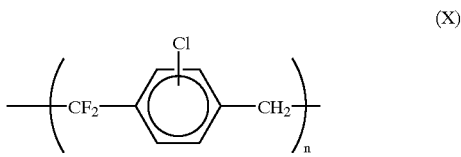

wherein n means degree of polymerization.

* * * * *

UNITED STATES PATENT AND TRADEMARK OFFICE
CERTIFICATE OF CORRECTION

PATENT NO. : 6,194,620 B1
DATED : February 27, 2001
INVENTOR(S) : Hiroshi Maruyama It is certified that error appears in the above-identified patent and that said Letters Patent is hereby corrected as shown below:

Title page.
Item [54] should read:
-- DICHLORO-TETRAFLUORO -[2,2]-PARACYCLOPHANE, A PROCESS FOR MANUFACTURING THEREOF AND POLY-A, A-DIFLUORO-CHLORO-PARA-XYLYLENE FILM PREPARED THEREFROM --.

Signed and Sealed this

Eleventh Day of September, 2001

Attest:

NICHOLAS P. GODICI
Acting Director of the United States Patent and Trademark Office Attesting Officer